(12) United States Patent
Paschke

(10) Patent No.: US 8,961,176 B2
(45) Date of Patent: Feb. 24, 2015

(54) ULTRASONIC TOOL

(71) Applicant: Westdale Holdings LLC, Timonium, MD (US)

(72) Inventor: Richard Paschke, Timonium, MD (US)

(73) Assignee: American Eagle Instruments, Inc., Missoula, MT (US)

( * ) Notice: Subject to any disclaimer, the term of this patent is extended or adjusted under 35 U.S.C. 154(b) by 0 days.

(21) Appl. No.: 13/624,352

(22) Filed: Sep. 21, 2012

(65) Prior Publication Data

US 2013/0071812 A1 Mar. 21, 2013

Related U.S. Application Data

(60) Provisional application No. 61/537,315, filed on Sep. 21, 2011, provisional application No. 61/559,946, filed on Nov. 15, 2011.

(51) Int. Cl.
*A61C 17/20* (2006.01)
*A61C 1/07* (2006.01)
*A61C 13/20* (2006.01)

(52) U.S. Cl.
CPC .. *A61C 1/07* (2013.01); *A61C 13/20* (2013.01)
USPC .......................................... 433/119; 433/117

(58) Field of Classification Search
CPC .............. A61C 3/00; A61C 3/03; A61C 1/07; A61C 1/148; A61C 17/16; A61C 17/20
USPC ............ 433/27, 86, 118–119, 143, 144, 146, 433/117; 606/169
See application file for complete search history.

(56) References Cited

U.S. PATENT DOCUMENTS

| | | | | |
|---|---|---|---|---|
| 3,419,776 A | * | 12/1968 | Kleesattel | 318/118 |
| 3,930,173 A | * | 12/1975 | Banko | 310/26 |
| 3,956,826 A | | 5/1976 | Perdreaux, Jr. | |
| 4,321,039 A | * | 3/1982 | Schuss et al. | 433/82 |
| 5,567,153 A | | 10/1996 | Foulkes et al. | |
| 5,775,901 A | * | 7/1998 | Riso | 433/86 |
| 5,980,251 A | * | 11/1999 | Sullivan et al. | 433/119 |
| 6,164,968 A | * | 12/2000 | Feine | 433/119 |
| 6,328,566 B1 | * | 12/2001 | Feine | 433/119 |
| 6,716,028 B2 | | 4/2004 | Rahman et al. | |
| 2002/0028421 A1 | * | 3/2002 | Schilling et al. | 433/119 |
| 2004/0126736 A1 | * | 7/2004 | Atkin et al. | 433/119 |
| 2004/0191724 A1 | * | 9/2004 | Rahman et al. | 433/119 |

* cited by examiner

*Primary Examiner* — Edward Moran
(74) *Attorney, Agent, or Firm* — Heslin Rothenberg Farley & Mesiti P.C.

(57) ABSTRACT

An ultrasonic instrument includes a tip portion, a transducer configured to convert electrical energy into vibrational energy, an acoustic transformer interconnecting the transducer and the tip portion, and a grip portion disposed at least partially about the acoustic transformer. The grip portion is coupled to the acoustic transformer via a resilient nodal coupling at a nodal region of the acoustic transformer. The resilient nodal coupling is configured to provide rotational and axial stability to the acoustic transformer.

21 Claims, 9 Drawing Sheets

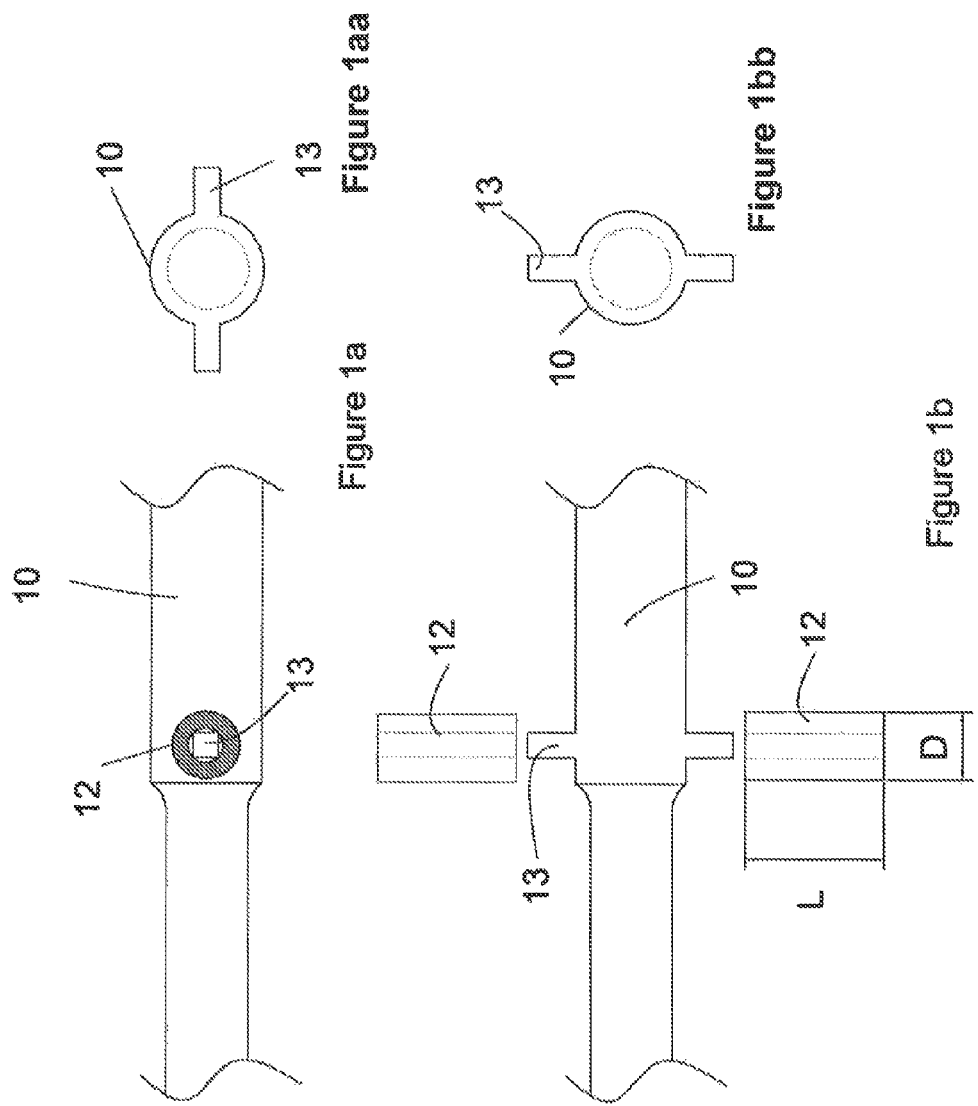

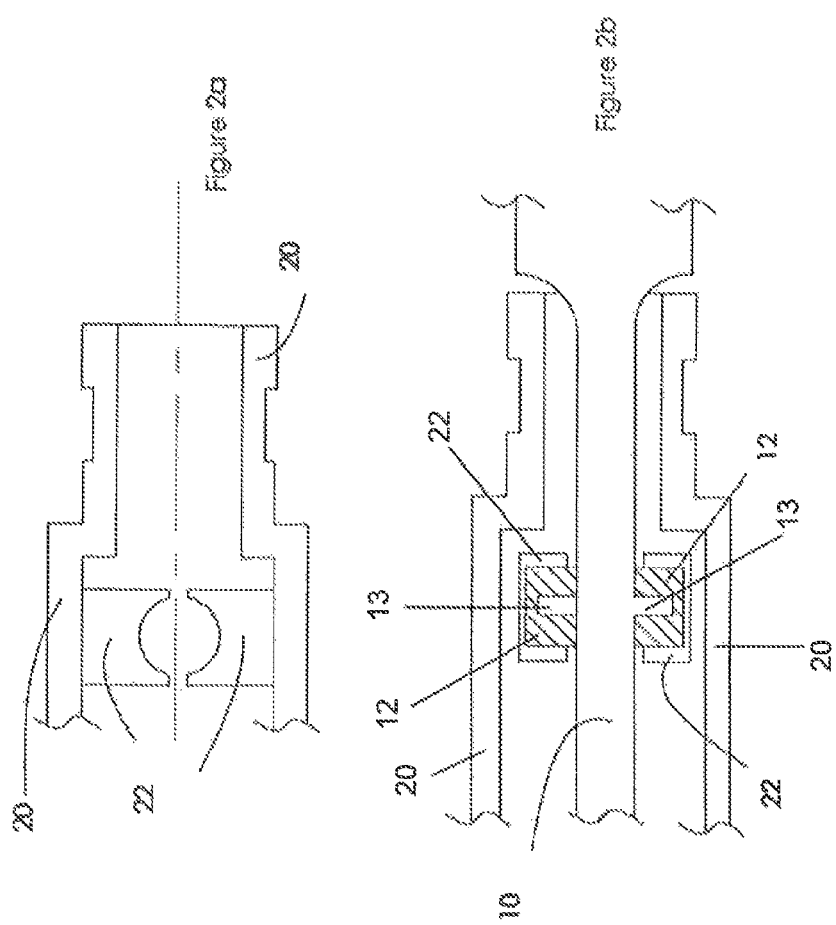

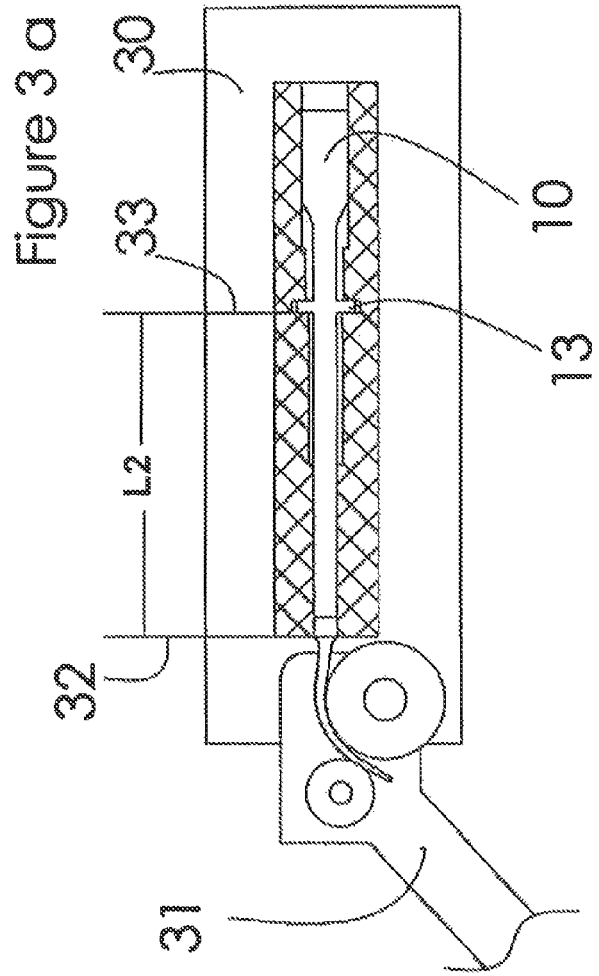
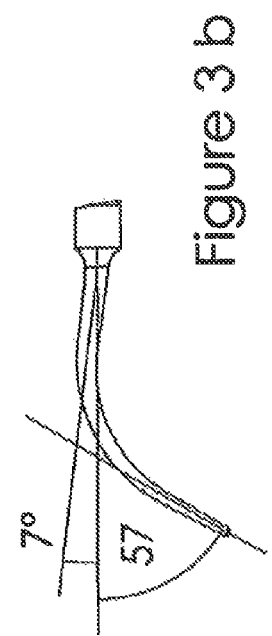

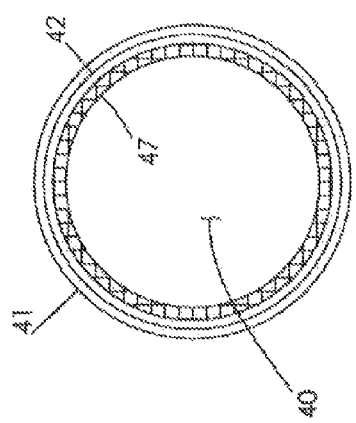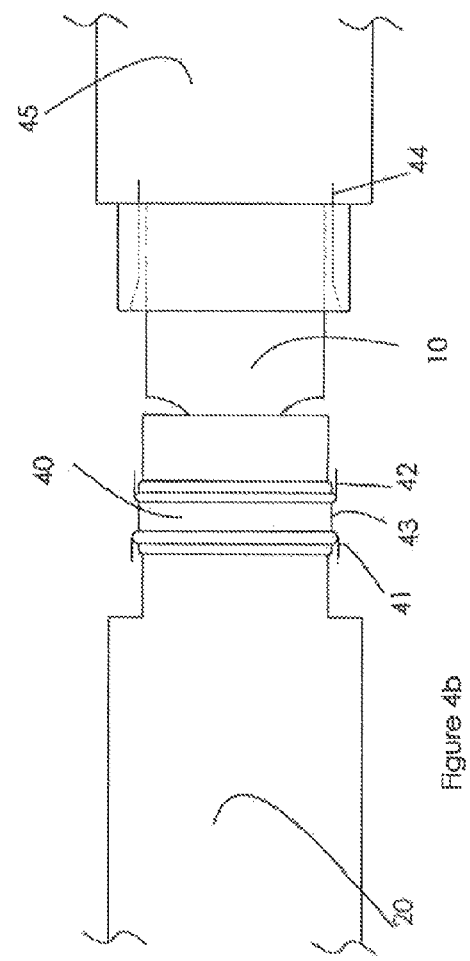

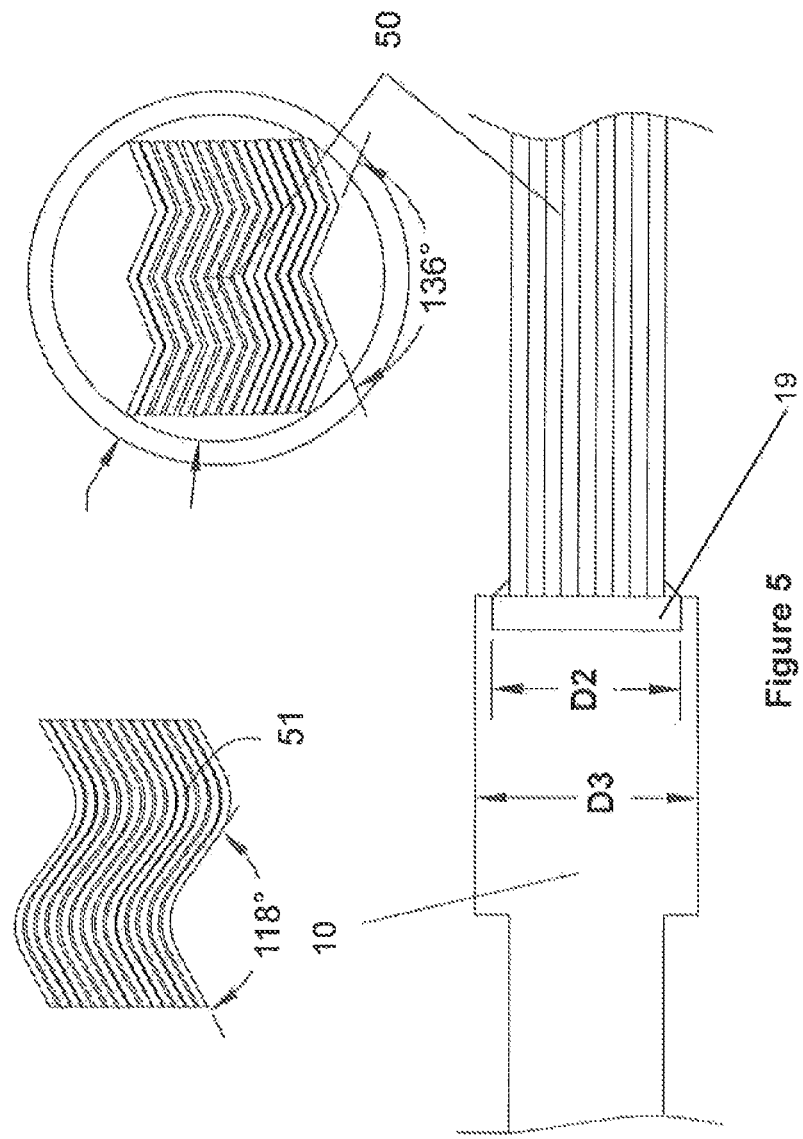

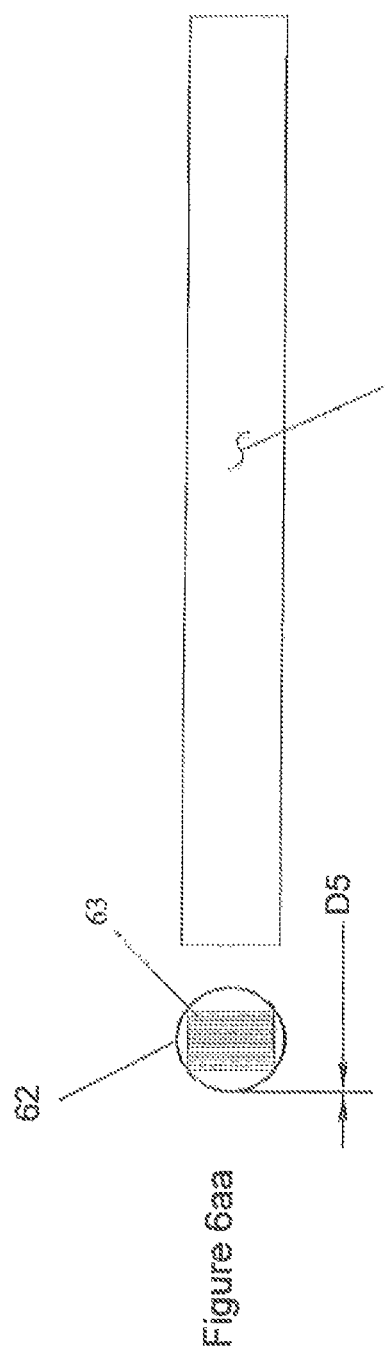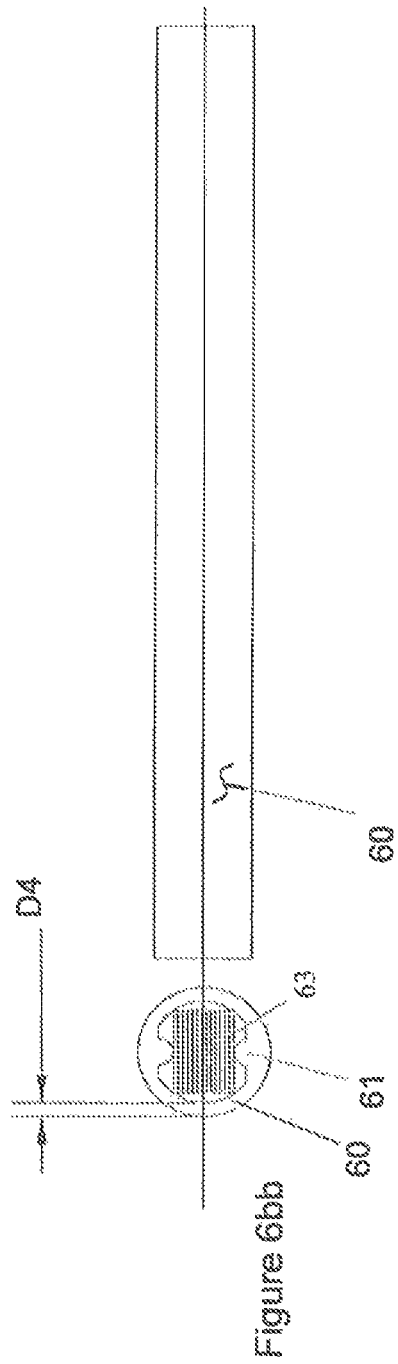

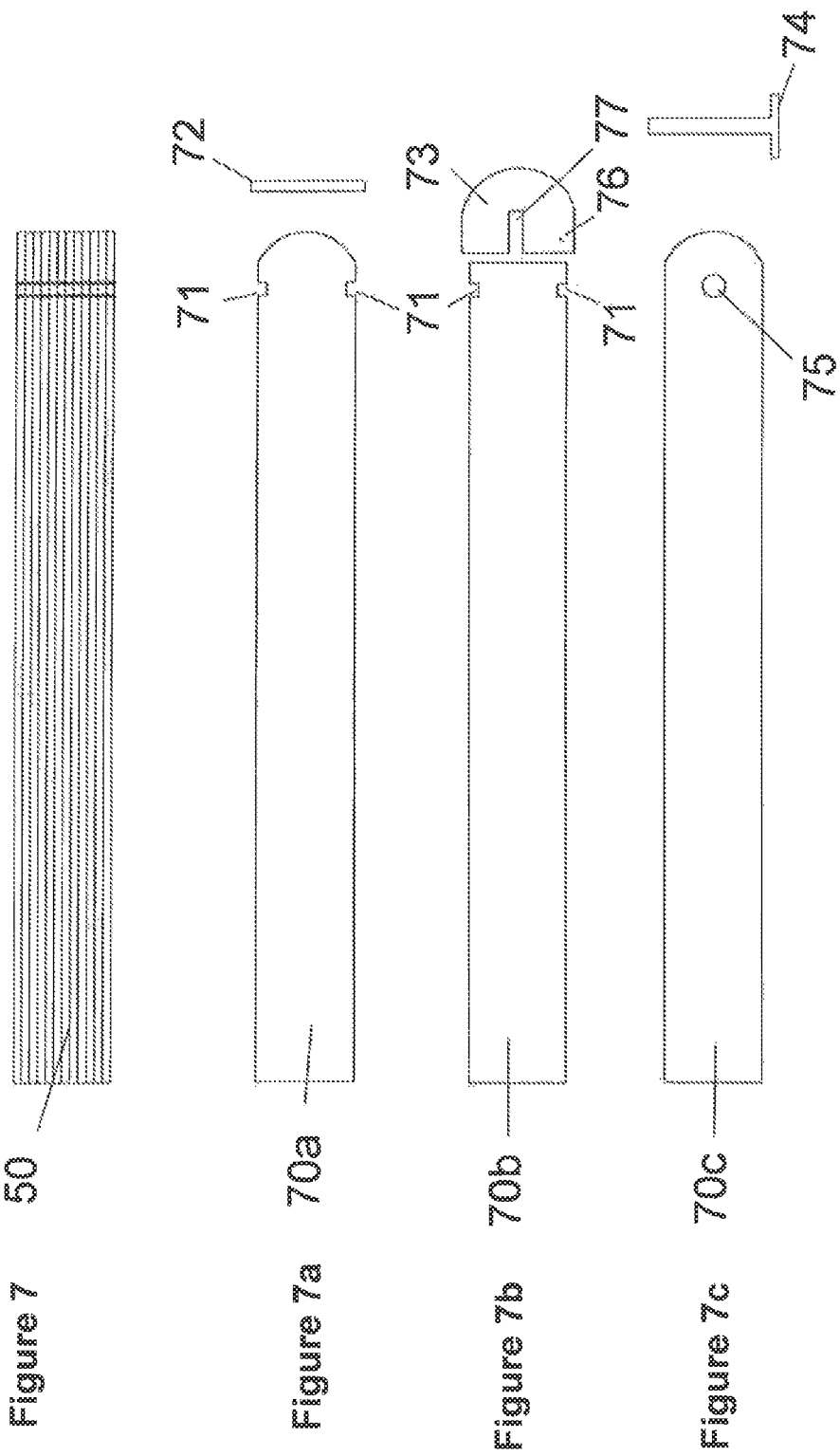

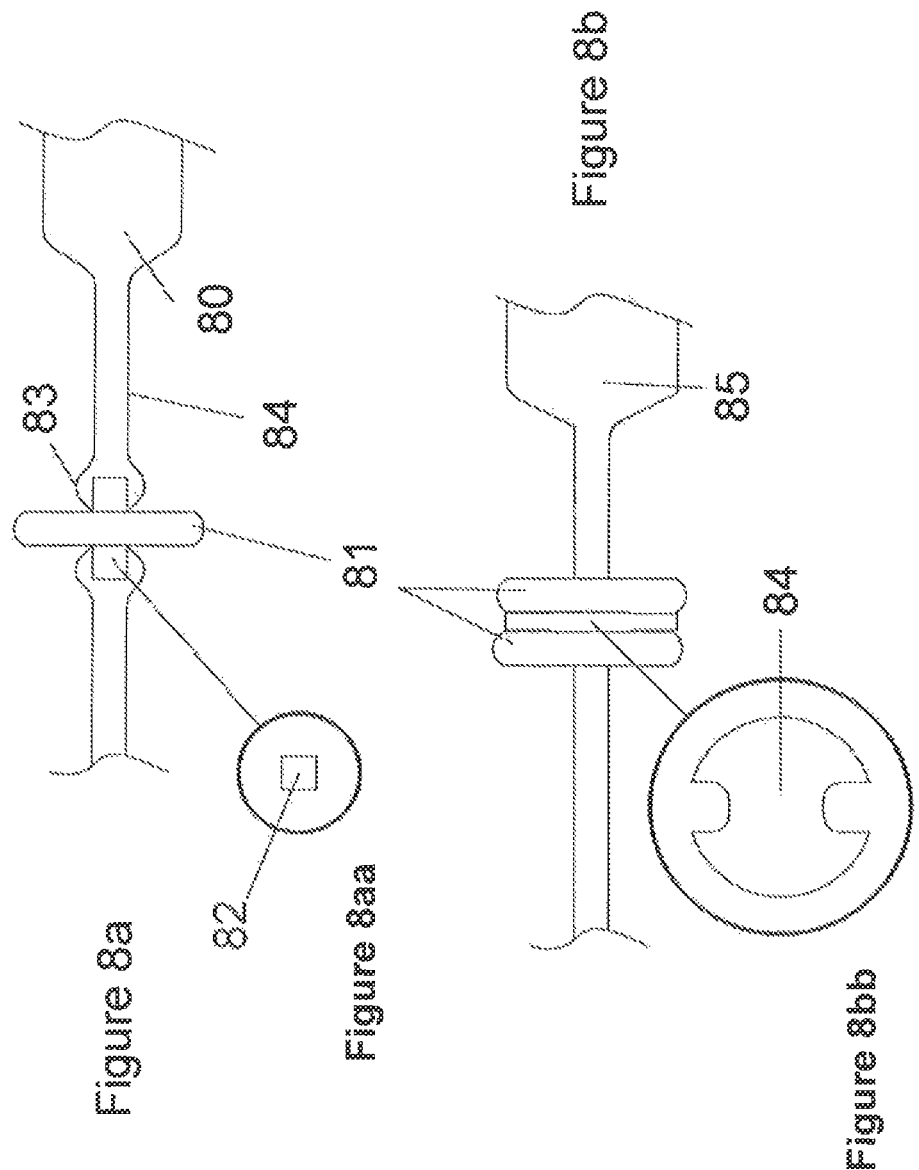

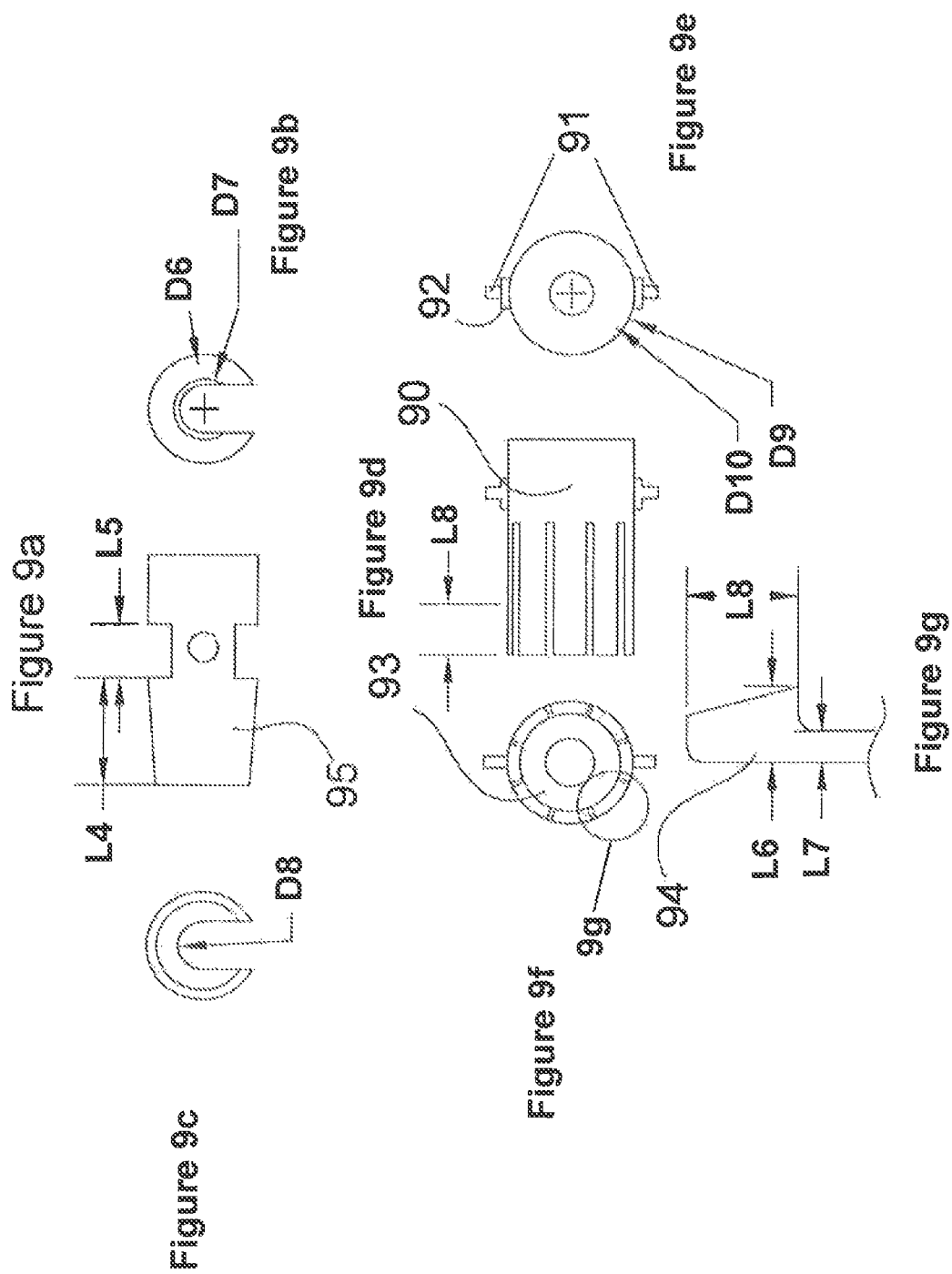

ULTRASONIC TOOL

CROSS-REFERENCE TO RELATED APPLICATIONS

This application claims the benefit of and priority to U.S. Provisional Patent Application No. 61/537,315, filed on Sep. 21, 2011, and U.S. Provisional Patent Application No. 61/559,946, filed on Nov. 15, 2011, the entirety each of which is incorporated by reference herein for all purposes.

BACKGROUND

1. Technical Field

The present disclosure relates to ultrasonic tools and, more particularly, to an ultrasonic tool, or insert, for use by dental professionals for dental treatments and procedures.

2. Background of Related Art

Ultrasonic dental tools, or inserts, generally include four basic parts. The primary part comprises a laminated stack of a magnetostrictive material, which is activated at its frequency of resonance to generate sufficient mechanical power. The second part is a specially shaped tip that makes contact with the treatment area. This tip provides access and adaptation to the treatment area. The third part is an acoustic transformer, often referred to as a connecting body, which connects the laminated stack to the tip. The fourth part is a grip, which allows the practitioner to hold and maneuver the insert during use.

Each of these building blocks for the insert has an important role in the operation of the insert. The stack provides the necessary power to drive the tip. The acoustic transformer matches the impedance of the stack to the tip, provides amplification of the mechanical motion generated by the stack, and delivers coolant and lavage to the tip. The tip transfers the mechanical motion to the treatment area, which is often a tooth or root surface. It also directs the lavage or coolant provided by the connecting body. The grip not only allows the practitioner to hold the insert but is a key component since it attaches to the acoustic transformer. It is therefore critical that the grip connect at a nodal point for the motion along the length of the acoustic transformer. Attachment to a point not on the node will dampen the motion and reduce the available power at the tip of the insert.

Cavitron® Corporation introduced ultrasonic inserts to the dental market in the late 1950's. The first inserts were called "P" types to differentiate them from the cutting inserts first used for cavity preparation. Similarly as used today, the basic structure and design of these first inserts included four basic components: a laminated stack of a magnetostrictive material, a working tip, an acoustic transformer or connecting body that connects the tip to stack, and a grip allowing the practitioner to hold the insert during use.

These original Cavitron® designs adapted a surgical steel tube to deliver water to the treatment area. Straight Permanickel® laminations were used to generate the mechanical energy. An acoustic transformer amplified the mechanical motion generated by the stack, and a metal grip was attached to the connecting body using a compressed O-ring.

Over the years, improvements have been in the areas of water delivery to the treatment area. U.S. Pat. No. 3,930,173 to Banko and U.S. Pat. No. 5,567,153 to Foulkes et al. describe examples of the use of non-concentric holes in the tip of the insert. A swivel feature that allowed the practitioner to more easily rotate and adapt the tip along the line angles of teeth is described in U.S. Pat. No. 6,716,028 to Rahman et al. This design forced a compromise between the ease of rotation (generally rotational torque below 1 in-lb.) and leakage. At lower torque levels, the risk of coolant water leakage at the point of rotation was increased. Some designs utilize the slippage of the O-ring that seals the insert in the handpiece. These designs use a traditional toroid O-ring that seals both the handpiece-insert interface and provides a low torque rotation. They typically allow rotation within the gland area of the O-ring but are at the mercy of O-ring quality, dimensional tolerances of the O-ring, and handpiece dimensions to provide a good seal over all operating conditions.

Early inserts also had the disadvantage of loosening of the attachment of the grip to the insert after several sterilization cycles. Retightening was possible but alignment of the water tubing while retightening was problematic. In addition, the tightness of the capture mechanism often resulted in instability of the grip in both the lateral and longitudinal planes. Later designs used surface indentations to minimize loosening, but these designs did not address the problems of rotational and axial movement of the grip during use. U.S. Pat. No. 3,956,826 to Perdreaux describes a method of capturing the connecting body inside a cavity in a resin grip. While this eliminates rotational and axial instability, it results in a hard mount of the connecting body at the nodal point. The end result is an improvement in the stability of the grip but degradation in the tip motion caused by the hard mounting of the grip to the connecting body. A hard mount also increases the transfer of ultrasonic energy from the connecting body to the grip.

The original stack configuration for the Cavitron designs was a flat lamination without any added rigidity either along the length of the stack or in the cross-section. Some manufacturers added a "c" shape to the stack but this added little rigidity to the stack assembly, while other manufacturers added a "v" shape to the stack and glued the laminations together. While this approach added rigidity to the stack, bend angles less than 100 degrees introduced increased stress to the laminations and moved the center of gravity of the stack assembly off the concentric line of the stack-connecting body junction.

The stack assembly in typical ultrasonic dental inserts is brazed at both ends. The distal end has an end-ball attached to hold the ends of the laminations together and provide a rounded surface to minimize any damage to the handpiece during insertion and removal. U.S. Pat. No. 5,980,251 to Sullivan et al., for example, describes a method of creating a conductive connection of brazing material (silver solder) at both ends of the stack. First, this is counterproductive in that it increases the losses in the stack assembly during use. Second, it decreases the frequency of resonance of the stack assembly because of the lower sound velocity of the brazing material compared to the Permanickel® laminations. Third, the phase shift of the feedback signal in ultrasonic systems is adversely affected, especially with regard to those systems employing motional or velocity feedback.

SUMMARY

In accordance with the present disclosure, an ultrasonic dental tool, or insert, is provided. The insert includes a notch on both sides of the distal end of the laminated stack assembly. The notches are secured in any suitable fashion, e.g., using a high temperature heat shrinkable material.

In embodiments, the distal end of the stack includes an end cap. The end cap may be a molded or machined high temperature resin that provides mechanical stability of the laminations during ultrasonic activation and sterilization cycles.

In embodiments, a non-metallic or low conductivity metal rivet component secures the laminations in the stack assembly. The component is secured in a small diameter hole near the distal end of the stack assembly by, for example, staking, snap locking, gluing, ultrasonic welding, etc.

In embodiments, a rigid or semi-rigid tube encloses the laminations in the stack assembly. The tube may be constructed from a high temperature resin and/or may be formed via extruding or molding. This encasement, e.g., the tube, may further include a nodal support for the laminations at their midpoint.

In embodiments, a resilient material captures the connecting body in the nodal area. For example, a "soft mount" configuration for the grip may be provided, while also providing stability with minimal axial and rotational movement during use.

In embodiments, the laminated stack assembly may be recess mounted to the mesial end of the connecting body. Such a mounting allows for concentric mounting of the stack assembly to the connecting body, resulting in minimum brazing material on the lateral sides of the stack assembly.

In embodiments, the laminations in the stack assembly define a pre-determined shape that provides adequate stiffness to the laminations to avoid deformation during use and handling of the insert.

In embodiments, the insert is rotatable 360 degrees during use with minimal torque. The use of a multi-diameter sealing component is also contemplated.

In embodiments, precise bending of the insert tip can be achieved at the location of the nodal point supports in a bending fixture.

Particular advantages and features of the above-mentioned and other embodiments of the present disclosure are described below. To the extent consistent, any or all of the above-mentioned embodiments (or any other embodiments) may be used in conjunction with any or all of the other embodiments described herein.

A typical stack comprises laminations of a Ferro-magnetic (magnetostrictive) material ranging from 0.007 to 0.010 inches thick. The industry standard size in dentistry is 0.010 inches. Thinner laminations are often used at frequencies higher than 25 kHz to reduce eddy-current losses. The laminated stack assemblies of an ultrasonic dental tool have the capability to outlast the tip and connecting body assemblies by a factor of 10 to 20 times. The endurance of the stack assemblies however, is limited by handling damage. The present disclosure provides a stack having both improved electro-mechanical characteristics and durability. In particular, the multiple angle bend of the stacks of the present disclosure, e.g., in the form of a "Z" bend or a "W" bend, provide both lateral and longitudinal rigidity to the laminations in the stack assembly without introducing excessive stresses along the bends because of the large bend angles. Bend angles are typically between 100 and 150 degrees. The basic geometry of the assemblies of the present disclosure place the center of the assembly on or close to the centerline of the connecting body-stack junction.

Typically, even slight bending of the stacks will result in a loss in mechanical output of the insert. A new stack that is bent by handling and then re-straightened will in most cases perform like an old insert with a tip worn beyond the recommended 2 mm length. The present disclosure provides a rigid or semi-rigid tubing to protect the stack during all phases of usage. The tubing can be an extruded or a machined piece with an internal dimension that approximates the diagonal dimension of the stack assembly. The mesial end of the tubing is configured to facilitate mounting the insert into a handpiece, provides a seal for the insert-handpiece interface, and allows for relatively low torque rotation of the insert assembly within the handpiece. In this configuration, the laminations on the stack assembly are flat and the distal ends of the laminations are not bound together. Further, in this configuration, a molded shell may be used in place of the tube. The advantages of the shell are the versatility of having several cross-sectional diameters and the addition of a nodal support for the stack assembly.

Currently, applications requiring insertion and removal from a handpiece often have interference due to the size and shape of the brazed end-ball. The present disclosure provides configurations that avoid the pitfalls of brazing the distal ends of the laminations together. This eliminates the possible interference fit into a dental handpiece due to an oversize endball. The use of a molded end cap, a heat shrinkable material, or a low conductivity pin improves assembly time and reduces the handling cost of the stack assembly without creating interference with the feedback system of the ultrasonic device.

Complete dental tools are customarily referred to as "half lambda" tools because they comprise two parts, where each part consists of a one-half wavelength (half lambda) as determined by the frequency of resonance of the materials and the physical lengths of the components. These tools are free to move at both ends and have two centrally located longitudinal nodal points. By definition, the longitudinal motion at the nodes is zero. Any contact of the tool off the nodal points will result in damping of the motion. Accordingly, the present disclosure provides a dental tool that mounts the grip to the connecting body with a resilient nodal mount (referred to herein as a "soft mount"). One of the key features of this configuration is that it minimizes the loading effects caused by the shifting of the nodal point during loading of the tool's tip. This configuration also minimizes the transfer of ultrasonic energy to the grip because of the high impedance presented by the resilient nodal support. Several variations of the soft mount are described in greater detail hereinbelow. For example, in embodiments, protrusions are located on the connecting body in the nodal region. An extruded resilient material is placed onto these protrusions and the assembly is placed into the insert grip. Alternatively or additionally, in embodiments, commercially available resilient O-rings or similar components may be utilized to provide a soft mount between the connecting body and the grip. The capture mechanisms for the nodal supports can be machined or molded.

Precise bending of the tips on the connecting body assemblies requires a reliable registration point in the bending fixtures. Current insert designs rely on the edge of the tip shank, but these points are located on radii and require the operator to use an approximate reference point. The present disclosure uses nodal protrusions on the connecting body assembly to precisely register the connecting body in a bending fixture. This configuration allows for the interchanging of bending tool inserts for bending of different tip styles and lengths of the assemblies.

The grip of an insert tool provides the practitioner the ability to grasp and maneuver the tool during use. The present disclosure provides a configuration that facilitates the rotation and adaptation of the working tip along the line angles of the tooth. One of the limitations for all resin grips is the small cross-sectional area in the gland area of the O-ring. This small cross-section causes problems in fluid flow across this area during molding. The thin section also creates challenges in welding the molded grips together. To account for this, the present disclosure provides a flat seal with or without raised circumferential rings, which allows the use of a thicker cross-section in the insert grip gland area. The mounting area can be shaped to allow smooth interfaces for the seal of the insert and a profile for the center of the seal that enhances both the ability to seal the insert-handpiece interface and provide a low torque rotation.

Dental handpieces typically have a cross-section that allows for mounting of a dental tool or insert with minimal space allowed for water delivery to the insert. When the brazed joint of the stack-connecting body is too large, it impedes the entry of the insert into the handpiece. This can result in reduced mechanical output at the tip due to the damping effect when a portion of the stack assembly is loaded off the nodal point. It can also restrict the water flow to the insert resulting in ejection of the insert due to backpressure in the handpiece. This is aggravated with the use of the aforementioned toroid O-ring in rotational designs. The present disclosure provides a connecting body with a recessed area that self-aligns the connecting body and stack assembly during assembly. A further feature of this configuration is that it provides an area for a braze fillet, thereby minimizing the possibility of excessive braze material at the joint.

BRIEF DESCRIPTION OF THE DRAWINGS

FIG. 1a is a side view of a connecting body provided in accordance with the present disclosure and including two protrusions at the nodal point with a resilient material placed over the protrusions;

FIG. 1aa is a transverse, cross-sectional view of FIG. 1a taken at the nodal point;

FIG. 1b is a top view of the connecting body of FIG. 1a illustrating the positioning of the resilient material over the protrusions;

FIG. 1bb is a transverse, cross-sectional view of FIG. 1b taken at the nodal point;

FIG. 2a is a side view of the connecting body of FIG. 1a shown captured by the insert grip;

FIG. 2b is a top view of the connecting body of FIG. 1a shown captured by the insert grip;

FIG. 3a is longitudinal, cross-sectional view of a bending tool using nodal supports to register the connecting body for precise bends;

FIG. 3b illustrates exemplary bending geometry of the bending tool of FIG. 3a;

FIG. 4a is a transverse, cross-sectional view of a multi-level seal for the insert interface with the dental handpiece;

FIG. 4b is a top view of the insert and dental handpiece including the multi-lever seal of FIG. 4a disposed about the interface therebetween;

FIG. 5 illustrates laminations forming a stack assembly mounted in a countersink on the connecting body of FIG. 1a;

FIGS. 5a and 5b are transverse, cross-sectional view of various configurations of the laminations forming the stack assembly;

FIG. 6a is an illustration of a tubular member that mounts over the laminated stack assembly;

FIG. 6aa is a transverse, cross-sectional view showing the tubular member mounted over the laminated stack assembly;

FIG. 6b is an illustration of a two-piece molded sheath that mounts over the laminated stack assembly;

FIG. 6bb is a transverse, cross-sectional view showing the two-piece molded sheath mounted over the laminated stack assembly;

FIG. 7 is a top view of a notches laminated stack assembly;

FIG. 7a is an exploded, side view of the notched laminated stack assembly of FIG. 7 and an O-ring configured for engagement within the notches of the laminated stack assembly;

FIG. 7b is an exploded, side view of another embodiment of a notched laminated stack assembly and a cap configured for engagement about an end of the laminated stack assembly;

FIG. 7c is an exploded, side view of another embodiment of a notched laminated stack assembly and a cap configured for engagement about an end of the laminated stack assembly;

FIG. 8a illustrates the positioning of resilient nodal mounts on a connecting body without a flange;

FIG. 8aa is an enlarged front view of the nodal area shown in FIG. 8a;

FIG. 8b illustrates the positioning of multiple resilient nodal mounts on a connecting body with a flange;

FIG. 8bb is an enlarged front view of the disk shown in FIG. 8b;

FIG. 9a is an illustration of tapered cylinder for positioning a resilient mount on a connecting body; and FIG. 9b is a transverse, cross-sectional view in a first direction of the tapered cylinder of FIG. 9a;

FIG. 9c is a transverse, cross-sectional view in a second direction of the tapered cylinder of FIG. 9a;

FIG. 9d is a side view of a retaining component with anti-rotation tabs for use with the tapered cylinder of FIG. 9a;

FIG. 9e is a transverse, cross-sectional view in a first direction of the retaining component of FIG. 9d;

FIG. 9f is a transverse, cross-sectional view in a second direction of the retaining component of FIG. 9d; and FIG. 9g is an enlarged, side view of the area of detail indicated in FIG. 9f.

DETAILED DESCRIPTION

Particular embodiments of the present disclosure are described hereinbelow with reference to the accompanying drawings. In the following description, well known functions or constructions are not described in detail to avoid obscuring the present disclosure in unnecessary detail.

FIGS. 1a and 1aa illustrate a resilient nodal mount 12 and an acoustic transformer, or connecting body 10 having a pair of opposed protrusions 13. Resilient mounts 12 fit over the protrusions 13 to provide a "soft mount" to the nodal area of the connecting body 10. The preferred geometry of the protrusions 13 is square because this shape provides the smallest contact area between the protrusions 13 and the resilient mounts 12 and is also the easiest and least expensive to machine. However, other configurations are also contemplated. FIGS. 1b and 1bb illustrate the axial mounting of the resilient nodal mounts 12 onto the protrusions 13 of the connecting body 10. The length L and the diameter D of the resilient nodal mounts 12 are determined by the maximum diameter of the insert grip (FIGS. 2a-2b).

FIGS. 2a and 2b illustrate the mounting of the connecting body 10 within the grip 20. More specifically, FIG. 2a illustrates the nests 22 of the grip 20. As shown in FIG. 2b, the nests 22 are configured to capture the soft mount, e.g., the resilient nodal mounts 12 attached to the protrusions 13 of the connecting body 10. The soft mount assembly is totally contained within the nests 22. The area between the connecting body 10, the grip 20, and the nests 22 allows the flow of coolant fluid across the nodal mount.

FIG. 3a illustrates a bending tool holding fixture 30 for retaining the connecting body 10. An alignment distance L2 is defined between a registration point 33 and the beginning of the bending point 32. The bending arm 31 is shown in the stop position for the completed bend. The contra angle shown in FIG. 3b is achieved by moving the bending arm 31 upward to its vertical stop point (not shown).

An embodiment of the present disclosure for a low rotational torque insert is illustrated in FIGS. 4a and 4b, e.g., an insert requiring a rotational torque of between about 0.5 in-oz and about 1.5 in-oz. An elongated sealing gasket 40 having a body defining an internal diameter 47 is provided. The elongated sealing gasket 40 defines a relatively flat outer surface along its length and further includes a pair of circumferential rings defining outer diameters 42 and 41. The outer diameter 42 of one of the rings of the sealing gasket 40 when mounted in the gland area, e.g., recessed area, of the insert grip 20 is dimensioned to provide an easy insertion into a dental handpiece 45. This is because the outer diameter 43 is less than the inner diameter 44 of the dental handpiece 45. The outer diameter 41 is also greater than the outer diameter 42 of the sealing gasket 40. The low rotational torque of the insert grip 20 is achieved by the combination of the low friction between the circumferential rings defining outer diameters 41 and 42, and the internal diameter 44 of the dental handpiece 45. The outer diameters 41 and 42 also provide the required seal for the insert grip 20 when placed in the dental handpiece 45, during both static and dynamic phases of use. Although the sealing gasket 40 is shown with two circumferential rings, the low rotational torque function is contemplated with a single circumferential ring. It is also contemplated that the function can be achieved by using a sealing gasket 40 without additional circumferential rings, where the machining or molding of a seal gland controls the diameter 43 thereof to have a non-uniform diameter along its length.

With reference to FIGS. 5, 5a, and 5b, the present disclosure further provides for improved durability of a stack assembly (stack of laminations) 50, 51, e.g., Permanickel® laminations, although other laminations are also contemplated. Improved durability and improved electro-mechanical output is achieved by producing lamination shapes with a minimum of two bending angles (stack assembly 51 (FIG. 5a)) or three bending angles (stack assembly 50 (FIG. 5b)). The typical range for the angles can vary between 100 and 150 degrees. The preferred angles for the double-angle lamination stack assembly 51 are about 118 degrees, while the preferred angles for the triple-angle lamination stack assembly 50 is about 136 degrees, as shown in FIGS. 5a and 5b, respectively. The actual bending angles are in part determined by the required rigidity of the lamination, the thickness of the lamination, and the maximum final width of the bent lamination. The bend angles allow the stacking of 14 to 16 laminations inside the diameter D2 of the countersink 19 in connecting body 10, depending on the thickness of the individual laminations comprising the stack assemblies 50 and 51. The proximal end diameter D3 of connecting body 10 is limited by the minimum inside diameter 44 of the dental handpiece 45 (see FIG. 4b).

A further embodiment of this disclosure provides components 62, 60 for housing the stack assembly, e.g., stack assembly 63, as is illustrated in FIGS. 6a, 6aa, 6b, and 6bb. The use of a hollow extruded tube 62 or a two-part molded sheath component 60 eliminates the need for special shapes to the laminations. The component 62, 60 covers the stack assembly 63 and attaches to the grip 20 (FIG. 4b). In the case of the component 60, nodal supports 61 are molded at the approximate midpoint of the stack assembly 63, e.g., the nodal area thereof. This adds additional rigidity to laminations smaller than 0.010 thick. The component material's molding and welding requirements determine its thickness. Diameter D4 of sheath component 60 is selected to interface with the diagonal of the stack assembly 63, such that the outer edges of the stack assembly 63 make contact with the sheath component 60. Diameter D5 is dimensioned to assure non-interference fit of tube 62 into inner diameter 44 of handpiece 45 (see FIG. 4b). It is also contemplated that molded sheath 60 have multiple diameters facilitating inclusion of an interface sealing gasket 40 (see FIG. 4b).

Referring to FIGS. 7 and 7a-7c, also provided in accordance with the present disclosure are embodiments configured to eliminate the end brazing on the stack assembly, e.g., stack assembly 50 (or any other suitable stack assembly), without creating high conductivity connections. For example, as shown in FIG. 7a, in one embodiment, the distal ends of the laminations 70a of the stack assembly are rounded and notches 71 are stamped, typically 0.100 inches, from the rounded end. The laminations 70a are placed in a stack and a high temperature heat shrinkable material, e.g., ring 72, is applied to the notched area to secure the distal end of the stack. In another embodiment, as shown in FIG. 7b, the laminations 70b are notched but not rounded. The laminations 70b are placed in a stack and the distal ends are secured by placement of a cap 73. Cap 73 is configured with tabs 76 that provide a snap fit to the notches 71. Cap 73 has slots 77 to facilitate attachment about the stack of laminations 70b. A further embodiment, as shown in FIG. 7c, includes laminations 70c having a relatively small diameter hole 75 extending through the center of the radius of the distal ends of the laminations 70c. A component 74, e.g., a rivet, is inserted into hole 75 and is secured therein in any suitable fashion, e.g., deformation of component 74, gluing, ultrasonic welding, etc. The rivet may be formed from a low conductivity material.

A further embodiment of the present disclosure is illustrated in FIGS. 8a-8bb. The use of resilient mounts as nodal supports requires both axial and rotational stability of the insert grip. In one embodiment, as shown in FIG. 8a, connecting body 80 has a nodal area machined with multiple flat surfaces, shown for illustration as a square area 82 (FIG. 8aa). The lead in surfaces to the nodal area 82 are shown as raised areas 83 where the diameter of the raised areas 83 is greater than the diameter of connecting body 80 in area 84. The raised areas 83 facilitate the positioning of O-ring 81 at the nodal area 82. In combination, O-ring 81, nodal area 82, and raised areas 83 of the resilient nodal mount provide axial and rotational stability. In another embodiment, as shown in FIG. 8b, the nodal area on connecting body 85 includes a disk 84 defining a pair of slots (see FIG. 8bb). Disk 84 is sandwiched by O-rings 81, which in combination comprise a resilient nodal mount and provide axial and rotational stability.

A further embodiment of a resilient nodal mount provided in accordance with the present disclosure is shown in FIGS. 9a-9g. In particular, the mount comprises a tapered cylinder 95 (FIG. 9a) and a retainer 90 (FIG. 9b). This configuration is designed to compress and retain the O-rings 81 (FIGS. 8a and 8b). With additional reference to FIG. 8b, tapered cylinder 95 is modified by machining a slot on the underside thereof (see FIGS. 9b and 9c) to allow tapered cylinder 95 to be inserted over connecting body 85 for retention of O-rings 81. More specifically, two O-rings 81 are placed on connecting body 85 on both sides of disk 84. Tapered cylinder 95 is placed between the distal O-ring 81 and the large section of connecting body 85. Retainer assembly 90 is then placed over the tip end of connecting body 85 and slid into position to capture tapered cylinder 95. Retainer 90 is moved axially toward tapered cylinder 95 until fingers 94 on retainer 90 engage with the surface of tapered cylinder 95 that defines dimension L4 on tapered cylinder 95. Once aligned, retainer 90 is moved axially along connecting body 85 until O-rings 81 are compressed and fingers 94 snap into position within a recess defining dimension L5 on tapered cylinder 95. The compression surface for the O-rings 81 on tapered cylinder 95 is defined by the difference between diameters D6 and D7 (see FIG. 9*b*). In cases where the greater concentricity of the assembled parts is necessary, an inverted split washer with an inner diameter of D7 and an outer diameter of D6 is placed between tapered cylinder 95 and O-ring 81. Diameter D8 provides clearance between connecting body 85 and tapered cylinder 95. Shoulder 92 on retainer 90 provides clearance between assembly comprising retainer 95 and tapered cylinder 90 when mounted in grip 20 of handpiece 45 (see FIG. 4*b*).

In considering assembly of the resilient nodal mount of FIGS. 9*a*-9*g* onto connecting body 80 (FIG. 8*a*), tapered cylinder 95 is slid over the small diameter of connecting body 80 with the tapered end with diameter D6 facing the distal (tip) end of connecting body 80. An O-ring 81 is placed in the nodal area 82 and the retainer 90 is slid over the tip of the insert, with tabs 91 facing the distal (tip) end of connecting body 80. Flanges 94 on retainer 90 are aligned to make contact with the tapered edge of tapered cylinder 95. The retainer 90 and the tapered cylinder 95 are locked together when dimension L6 on flange 94 snaps into the gap L5 on tapered cylinder 95. Dimension L7 on flange 94 is dimensioned to allow dimension L6 on flange 94 to spread as it interfaces with tapered cylinder 95. The dimension L8 of flange 94 is less than the gap L5 on tapered cylinder 95 allowing the flange to snap into place. When locked together, the tapered cylinder 95 and retainer 90 compress the O-rings 81, providing a resilient mount for connecting body 80 when placed into grip 20 of handpiece 45 (see FIG. 4*b*). Tabs 91 on retainer 90 provide a secure mounting to the grip 20 of handpiece 45 (see FIG. 4*b*) with axial and rotational stability. Shoulder 92 provides a positive stop for mounting to allow the flow of water past the dimension D9 on retainer 90. Dimensions D8 is based on the diameter of the connecting body that is receiving the resilient mount. Typical dimensions for D8 are 0.145 to 0.155 inches. The compression surface on tapered cylinder 95 for O-ring 81 is defined by the difference between dimensions D6 and D7. The compression surface 93 on retainer 90 is defined by the difference in dimensions D10 and D9.

From the foregoing and with reference to the various figure drawings, those skilled in the art will appreciate that certain modifications can be made to the present disclosure without departing from the scope of the same. While several embodiments of the disclosure have been shown in the drawings, it is not intended that the disclosure be limited thereto as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An ultrasonic instrument, comprising:
   a tip portion;
   a transducer configured to convert electrical energy into vibrational energy;
   an acoustic transformer interconnecting the transducer and the tip portion, wherein said acoustic transformer comprises a pair of opposed protrusions defined at a nodal region; and
   a grip portion disposed at least partially about the acoustic transformer, the grip portion coupled to the acoustic transformer via a soft mount comprising a resilient nodal coupling at a nodal region of the acoustic transformer, the resilient nodal coupling comprising:
   a pair of resilient mounts in the form of resilient sleeves or rings disposed over the pair of opposed protrusions the nodal region of the acoustic transformer; and
   a nest defined within the grip, the nest configured to capture and totally contain the resilient mounts,
      wherein the resilient nodal coupling is structured to provide rotational and axial stability to the acoustic transformer by minimizing lateral and longitudinal movement of the grip relative to the acoustic transformer during static and dynamic phases of use of the ultrasonic instrument, and
      wherein an area between the acoustic transformer, the grip, and the nest provides a pathway for coolant fluid to flow across the nodal coupling.

2. The ultrasonic instrument according to claim 1, wherein the resilient mounts apply a holding force to the acoustic transformer.

3. The ultrasonic instrument according to claim 1, wherein the grip is formed at least partially from plastic.

4. An ultrasonic instrument, comprising:
   a tip portion;
   a magnetostrictive transducer configured to convert electrical energy into vibrational energy, the transducer formed from a plurality of laminations, each lamination configured to define a plurality of bending angles along a width dimension thereof, each lamination defining a length substantially equal to one-half wavelength at an operating frequency of the ultrasonic instrument; and
   an acoustic transformer interconnecting the transducer and the tip portion, the tip portion and the acoustic transformer cooperating to define a length substantially equal to one-half wavelength at the operating frequency of the ultrasonic instrument, wherein the acoustic transformer comprises a pair of opposed protrusions defined at a nodal region of the acoustic transformer; and
   a grip portion disposed at least partially about the acoustic transformer, the grip portion coupled to the acoustic transformer via a soft mount comprising a pair of resilient mounts in the form of resilient sleeves or rings disposed over the pair of opposed protrusions and a nest defined within the grip to capture and totally contain the resilient mounts, forming a resilient nodal coupling at a nodal region of the acoustic transformer, the resilient nodal coupling structured to provide rotational and axial stability to the acoustic transformer by minimizing lateral and longitudinal movement of the grip relative to the acoustic transformer during static and dynamic phases of use of the ultrasonic instrument, wherein an area between the acoustic transformer, the grip, and the nest provides a pathway for coolant fluid to flow across the nodal coupling.

5. The ultrasonic instrument according to claim 4, wherein the acoustic transformer defines a countersink at a proximal end thereof, the transducer configured for receipt within the countersink to substantially align the acoustic transformer relative to the transducer.

6. The ultrasonic instrument according to claim 4, wherein each lamination defines two bending angles, each bending angle equal to about 118 degrees.

7. The ultrasonic instrument according to claim 4, wherein each lamination defines three bending angles, each bending angle equal to about 136 degrees.

8. The ultrasonic instrument according to claim 4, wherein each lamination defines a slot towards a distal end thereof, and wherein an end cap is disposed about the distal ends of the laminations and engaged within the slots to secure the laminations to one another.

9. The ultrasonic instrument according to claim 8, wherein the end cap is shaped to substantially conform to a shape of the distal ends of the laminations.

10. The ultrasonic instrument according to claim 4, wherein the transducer is encased within a sheath, and wherein an outer surface of the transducer is tangent to an inner diameter of the sheath.

11. The ultrasonic instrument according to claim 10, wherein the sheath is formed from a hollow extruded tubular member.

12. The ultrasonic instrument according to claim 10, wherein the sheath is a cylindrical sheath and the sheath is formed from a first part and a second part, and the sheath includes a nodal support located substantially in a nodal area of the transducer.

13. An ultrasonic instrument, comprising:
a tip portion;
a transducer configured to convert electrical energy into vibrational energy;
an acoustic transformer interconnecting the transducer and the tip portion;
a grip portion disposed about a portion of the acoustic transformer, the acoustic transformer comprising a pair of opposed protrusions, the grip portion coupled to the acoustic transformer via a soft mount comprising a pair of resilient mounts in the form of resilient sleeves or rings disposed over the pair of opposed protrusions forming a resilient nodal coupling at a nodal region of the acoustic transformer, and a nest defined within the grip to capture and totally contain the resilient mounts, the grip portion defining a gland area, wherein an area between the acoustic transformer, the grip, and the nest provides a pathway for coolant fluid to flow across the nodal coupling;
a handpiece disposed about a remaining portion of the acoustic transformer such that the grip portion and the handpiece cooperate to fully enclose the acoustic transformer, the handpiece defining an engagement area are configured to receive the gland area of the grip portion; and
an elongated sealing assembly interdisposed between the gland area of the grip portion and the engagement area of the handpiece to rotatably and sealingly couple the grip portion and the handpiece to one another, wherein an outer surface of the elongated seal assembly comprises an outer surface of the ultrasonic instrument.

14. The ultrasonic instrument according to claim 13, wherein the elongated sealing assembly includes an elongated sealing gasket defining a first end portion, a second end portion, and a central portion extending between the first and second end portions, and wherein a diameter of at least one of the first and second end portions is greater than a diameter of the central portion.

15. The ultrasonic instrument according to claim 14, wherein at least a portion of the engagement area of the handpiece defines an internal diameter greater than the diameter of the central portion of the sealing gasket.

16. The ultrasonic instrument according to claim 13, wherein the elongated sealing assembly comprises an elongated sealing gasket wherein a first portion of the elongated sealing gasket comprises at least one ring member, a diameter of the first portion of the elongated sealing gasket is greater than a diameter of a second portion of the elongated sealing gasket, wherein the second portion of the elongated sealing gasket does not comprise at least one ring member.

17. The ultrasonic instrument according to claim 16, wherein the elongated sealing assembly further comprises a third portion, wherein the third portion comprises at least one ring member, a diameter of the third portion being greater than the diameter of the second portion, and the diameter of the third portion is not equal to the diameter of the first portion.

18. The ultrasonic instrument according to claim 13, wherein the grip portion is rotatable relative to the handpiece through 360 degrees of rotation.

19. The ultrasonic instrument according to claim 13, wherein a required torque for rotating the grip portion relative to the handpiece is between about 0.5 in-oz and about 1.5 in-oz.

20. The ultrasonic instrument of claim 1, wherein the pair of opposed protrusions are rectangular.

21. The ultrasonic instrument of claim 1, wherein the soft mount decouples ultrasonic energy in the acoustic transformer to the grip during static and dynamic phases of use of the ultrasonic instrument.

* * * * *